United States Patent
Lin et al.

(10) Patent No.: US 10,702,494 B2
(45) Date of Patent: Jul. 7, 2020

(54) METHOD FOR CANCER TREATMENT

(71) Applicant: Profeat Biotechnology Co., Ltd., Taoyuan (TW)

(72) Inventors: Tsun-Yuan Lin, Taoyuan (TW); Mu-Kuei Chen, Taoyuan (TW); Tsang-Tse Chen, Taoyuan (TW); Chai-Hui Fu, Taoyuan (TW); Hsun-Jin Jan, Taoyuan (TW); Wen-Cheng Chiu, Taoyuan (TW)

(73) Assignee: Profeat Biotechnology Co., Ltd., Taoyuan (TW)

( * ) Notice: Subject to any disclaimer, the term of this patent is extended or adjusted under 35 U.S.C. 154(b) by 232 days.

(21) Appl. No.: 14/476,136

(22) Filed: Sep. 3, 2014

(65) Prior Publication Data

US 2015/0065569 A1 Mar. 5, 2015

(30) Foreign Application Priority Data

Sep. 5, 2013 (TW) .............................. 10213975 A

(51) Int. Cl.
*A61K 31/295* (2006.01)
*A61K 31/198* (2006.01)
*A61K 35/00* (2006.01)
*A61P 35/00* (2006.01)

(52) U.S. Cl.
CPC .......... *A61K 31/295* (2013.01); *A61K 31/198* (2013.01); *A61P 35/00* (2018.01)

(58) Field of Classification Search
CPC ...... A61K 31/198; A61K 31/295; A61P 35/00
See application file for complete search history.

(56) References Cited

U.S. PATENT DOCUMENTS

| | | | |
|---|---|---|---|
| 2007/0270591 A1* | 11/2007 | Ashmead | .............. C07F 15/025 548/101 |
| 2009/0035385 A1* | 2/2009 | Bortz | ..................... A61K 31/19 424/604 |

FOREIGN PATENT DOCUMENTS

| | | |
|---|---|---|
| CN | 101102762 | 1/2008 |
| EP | 1658844 A1 | 5/2006 |
| EP | 2306187 | 4/2011 |
| EP | 2338495 | 6/2011 |
| FR | 2041 M | 9/1963 |
| WO | 9634602 A1 | 11/1996 |

(Continued)

OTHER PUBLICATIONS

Narendra P. Singh, et al., Selective toxicity of dihydroartemisinin and holotransferrin toward human breast cancer cells, 2001, Life Science, 70 49-56.

(Continued)

*Primary Examiner* — Theodore R. West
(74) *Attorney, Agent, or Firm* — Fishman & Associates, LLC

(57) ABSTRACT

The present invention is related to a method for cancer treatment comprising a step of administering to a subject in need thereof a therapeutically effective amount of a pharmaceutical composition comprising ferrous amino acid chelate and a pharmaceutically acceptable carrier. By means of amino acid chelating to ferrous and maintaining chelating state through the stomach, the pharmaceutical composition in accordance with the present invention would not cause any weight variation, and is suitable for inhibiting or treating cancer.

10 Claims, 4 Drawing Sheets

(56) References Cited

FOREIGN PATENT DOCUMENTS

WO      2003042404 A2    5/2003
WO      2008039421 A2    4/2008

OTHER PUBLICATIONS

Green, et al., Inhibition of Malignant Cell Growth by 311, a Novel Iron Chelator of the Pyridoxal Isonicotinoyl Hydrazone Class: Effect on the R2 subunit of Ribonucleotide Reductase, 2001, Clin Cancer Res 7:3574-3579.
Kato et al., Iron intake, body iron stores and colorectal cancer risk in women: a nested case-control study,1999, Int. J. Cancer: 80, 693-698.
Simonart, et al., Antiproliferative and Apoptotic Effects of Iron Chelatorson Human Cervical Carcinoma Cells, 2002, Gynecologic Oncology 85, 95-102.
Paola Ferrari et al., Treatment of mild non-chemotherapy-induced iron deficiency anemia in cancer patients: Comparison between oral ferrous bisglycinate chelate and ferrous sulfate, Biomedicine & Pharmacotherapy, 2012, vol. 66, pp. 414-418.
Supplementary European Search Report: EP13893164.

\* cited by examiner

METHOD FOR CANCER TREATMENT

BACKGROUND OF THE INVENTION

1. Field of the Invention

The present invention relates to a method for preparing a pharmaceutical composition comprising ferrous amino acid chelate, and more particularly the pharmaceutical composition comprising ferrous amino acid chelate relates to a method for cancer treatment.

2. Description of the Prior Arts

One of the main causes of death in world population is cancer or malignant tumor, wherein the mortality rates rank order is lung cancer, gastric cancer, liver cancer, colorectal cancer, breast cancer and cervical cancer. According to World Health Organization statistics (WHO), lung cancer mortality develops the fastest growing in the past two decades. Based on characteristics and clinical manifestations, lung cancers are classified into small cell lung cancer and non-small cell lung carcinoma (NSCLC). The occurrence of small cell lung cancer is higher in men, and is associated with smoking for 25%. Small cell lung cancer grows fast and spread easily via lymph or blood to other organs. NSCLC includes squamous cell carcinoma, adenocarcinoma, and large cell carcinoma and accounts for 75% lung cancer.

Squamous cell carcinoma is also called epidermoid carcinoma, common in male smokers, and mostly extends from local to outward at early spreads via blood trail at later stage. Adenocarcinoma is the most common type of lung cancer currently, clinical symptoms of adenocarcinoma often occur after metastasis distinctly, and lung cancers suffered by non-smokers are often adenocarcinoma. Large cell carcinoma has slower growth rate, but also spreads through the blood trail and lymphoid.

Small cell lung cancer is quite sensitive to chemical and radiation therapy, but most patients will relapse within two years and generate resistance after relieving treatment. Although NSCLC grows slowly, only a quarter of the cases can receive surgical treatment at early stage, and most cases are not sensitive to chemotherapy and radiation therapy. Based on the above reasons, lung cancer patients often have poor prognosis. In addition, since studies have shown that chemotherapy drugs tend to be an injury to the patient, and long-term use can cause lowered immunity, apoptosis of normal cell and lowered rate of survival. Therefore, a drug that is non-toxic to normal cells and can suppress lung cancer cell growth or apoptosis is currently in need.

In addition, liver cancer is of top ranked fatality. In addition to surgery, chemotherapy or radiation therapy often causes unbearable pain and side effects to patients. By means of inhibiting the mechanism of the progress of mutation, proliferation or spread, inhibiting hepatoma cells angiogenesis, promoting of hepatoma cells death or preventing hepatoma cell spread, target therapeutic agents are conventionally used to anti-liver cancer treatment. Moreover, since liver cancer expresses no obvious symptom at early stage, liver cancer prevention should get more attentions.

Singh et, al. (Life Science, 70 49-56, 2001) disclose that after incubation with holotransferrin, which increases the concentration of ferrous iron in cancer cells, dihydroartemisinin, an analog of artemisinin, effectively killed a type of radiation-resistant human breast cancer cell in vitro. Green et, al. (Clin Cancer Res 7:3574-3579, 2001) disclose that iron chelator (2-hydroxy-1-naphthylaldehyde benzoyl hydrazone) inhibited R2 subunit of ribonucleotide reductase to inhibit the growth of breast, bladder, and head and neck cancer cell lines. EP2306187 A1 discloses ferric iron composition comprising Fe (II) or Fe (III) can be used against breast cancer.

However, Kato et, al. (Int. J. Cancer: 80, 693-698, 1999) disclose increased body iron stores may increase the risk of colorectal cancer, possibly via catalyzing oxidation reactions. Simonart et, al. (Gynecologic Oncology 85, 95-102, 2002) disclose Desferrioxamine and deferiprone, two chemically unrelated iron chelators, induce a time- and dose-dependent inhibition of cervical carcinoma SiHa and HeLa cell growth, block certain cell types in the G0/G1 phase, and induce the apoptosis of these cells.

In summary, the prior art does not confirm whether iron or iron compounds have cancer inhibition or therapeutic efficacy. However, chemical drugs used to treat cancer, such as lung cancer or liver cancer, often have side effects and cause patient discomfort and lead to abandonment of the treatment. Therefore, pharmaceutical products for cancer treatment that have no side effects and can be absorbed by subject are a priority.

SUMMARY OF THE INVENTION

To overcome the shortcomings of chemical drugs for treating cancer causing side effect, the objective of the present invention is to provide a method for cancer treatment comprising a step of administering to a subject in need thereof a therapeutically effective amount of a pharmaceutical composition, wherein the pharmaceutical composition comprises ferrous amino acid chelate and a pharmaceutically acceptable carrier.

According to the present invention, the term "pharmaceutical composition comprising ferrous amino acid chelate" as used herein refers to a pharmaceutical composition comprising ferrous amino acid chelate made from mixing inorganic iron and amino acid.

Preferably, the inorganic iron includes, but is not limited to, ferrous sulfate, ferrous chloride and ferrous pyrophosphate.

Preferably, the amino acid is glycine.

Preferably, the pharmaceutical composition comprises ferrous amino acid chelate having 95 wt % to 100 wt % ferrous glycinate chelate. More preferably, the pharmaceutical composition comprises ferrous amino acid chelate having 98 wt % to 99.9 wt % ferrous glycinate chelate.

Preferably, the pharmaceutical composition comprises ferrous amino acid chelate prepared from mixing inorganic iron and amino acid through 60° C. to 90° C. and heating for 8 hours to 48 hours to obtain the pharmaceutical composition comprising ferrous amino acid chelate, wherein the weight ratio of inorganic iron and amino acid is between 1:1.2 and 1:1.5.

According to the present invention, the pharmaceutical composition comprises ferrous amino acid chelate as used herein, having at least one ferrous amino acid chelate, wherein the chelating ratio of ferrous and amino acid of the ferrous amino acid chelate is between 1:1 and 1:4. More preferably, the chelating ratio of ferrous and amino acid of the ferrous amino acid chelate is between 1:1.5 and 1:2.5.

Preferably, the pharmaceutical composition comprising ferrous amino acid chelate includes a reductant, wherein the reductant not only maintains the oxidation state of ferrous of the pharmaceutical composition comprising ferrous amino acid chelate, but also enhances intestinal absorption rate of subjects. The reductant includes, but is not limited to, ascorbic acid, citric acid, acetic acid, propionic acid, butyric acid, lactic acid, malic acid, sulfonic acid and succinic acid.

According to the present invention, the term "cancer treatment" as used herein refers to treating, relieving or inhibiting cancer. The term "therapeutically effective amount" as used herein, refers to a dosage to alleviate or inhibit progress of cancer. According to the present invention, the therapeutically effective amount for reducing, stopping, even inducing death of lung tumor or liver tumor, and the therapeutically effective amount for inhibiting lung tumor or liver tumor is determined by administering the pharmaceutical composition comprising ferrous amino acid chelate in a specific amount, and measuring the tumor volume in a specific period.

According to the present invention, the term "the pharmaceutically acceptable carriers" as used herein includes any physiologically compatible and all solvents, dispersion medium, antibacterial and antifungal agents, isotonic and absorption delaying agents and analogues thereof. For example, the pharmaceutically acceptable carriers include one or more water and combination of water, salt water, phosphate buffered saline (PBS), dextrose, glycerol, ethanol and its analogues. Preferable combination includes isotonic agents, for example, sugar or polyol such as mannitol, sorbitol, or sodium chloride. The pharmaceutically acceptable carriers further include microscale auxiliary substances such as wetting or emulsifying agents, preservatives or buffers.

Preferably, the therapeutically effective amount of the pharmaceutical composition comprising ferrous amino acid chelate is between 0.2 mg/kg/day and 15 mg/kg/day. More preferably, the therapeutically effective amount is between 0.3 mg/kg/day and 14 mg/kg/day. The most preferably, the therapeutically effective amount is between 0.4 mg/kg/day and 12 mg/kg/day.

In accordance with the present invention, the pharmaceutical composition for cancer treatment is prepared for multiple forms, includes, but is not limited to, liquid, semi-solid and solid dosage, and such as liquid solution (included injectable and infusible solution), dispersions or suspensions, tablets, pills, powders, liposomes and suppositories. Preferred form depends on the mode of administration and therapeutic application of expectations.

Preferably, the pharmaceutical composition of the present invention is administered orally or in the form of infusion solutions, and the preferred mode of administration is enteral modes, such as orally. In an embodiment of the present invention, the pharmaceutical composition comprising ferrous amino acid chelate is orally administrated.

Preferably, the pharmaceutical composition of the present invention further comprises excipient for enteral or parenteral dosage forms.

Preferably, the enteral dosage forms of the pharmaceutical composition of the present invention is oral dosage, includes, but is not limited to solutions, suspensions, tablets and capsules.

Preferably, the cancer of the present invention includes, but is not limited to melanoma, liver cancer, colon cancer, lung cancer, gastric cancer, esophageal cancer, breast cancer, prostate cancer, and leukemia.

More preferably, the cancer of the present invention includes, but is not limited to, brain tumor, low-grade astrocytoma, high-grade astrocytoma, pituitary adenoma, meningioma, CNS lymphoma, oligodendroglioma, craniopharyngioma, ependymoma, brain stem tumor, head and neck tumor, laryngeal cancer, oropharyngeal cancer, nasopharyngeal tumor, salivary gland tumor, hypopharyngeal cancer, thyroid cancer, oral cavity tumor, chest wall tumors, small cell lung cancer, non-small cell lung cancer (NSCLC), thymoma, mediastinal tumor, male breast cancer, abdomen-pelvis tumor, hepatoma, liver adenocarcinoma, gallbladder cancer, biliary tract cancer, pancreatic cancer, small intestinal tumor, large intestinal tumor, anal cancer, bladder cancer, renal cell carcinoma, cervix cancer, endometrial cancer, ovarian cancer, uterine sarcoma, and skin cancer.

More preferably, the cancer of the present invention is liver cancer or lung cancer.

By means of amino acids of small molecular weight chelating to ferrous and maintaining chelating state through the stomach, the advantage of the pharmaceutical composition in accordance with the present invention is that such pharmaceutical composition can be easily absorbed for subject and would not cause any weight variation as demonstrated by the present invention. Further, the pharmaceutical composition comprising ferrous amino acid chelate of the present invention has better ability for inhibiting or relieving lung or liver tumors compared to the commercial ferrous amino acid (such as Ferrochel®) and inorganic iron (such as ferrous sulfate). Therefore, the pharmaceutical composition comprising ferrous amino acid chelates of the present invention can be used for inhibiting or relieving cancer, particularly lung or liver cancer.

DETAILED DESCRIPTION OF THE PREFERRED EMBODIMENTS

Figure 1:
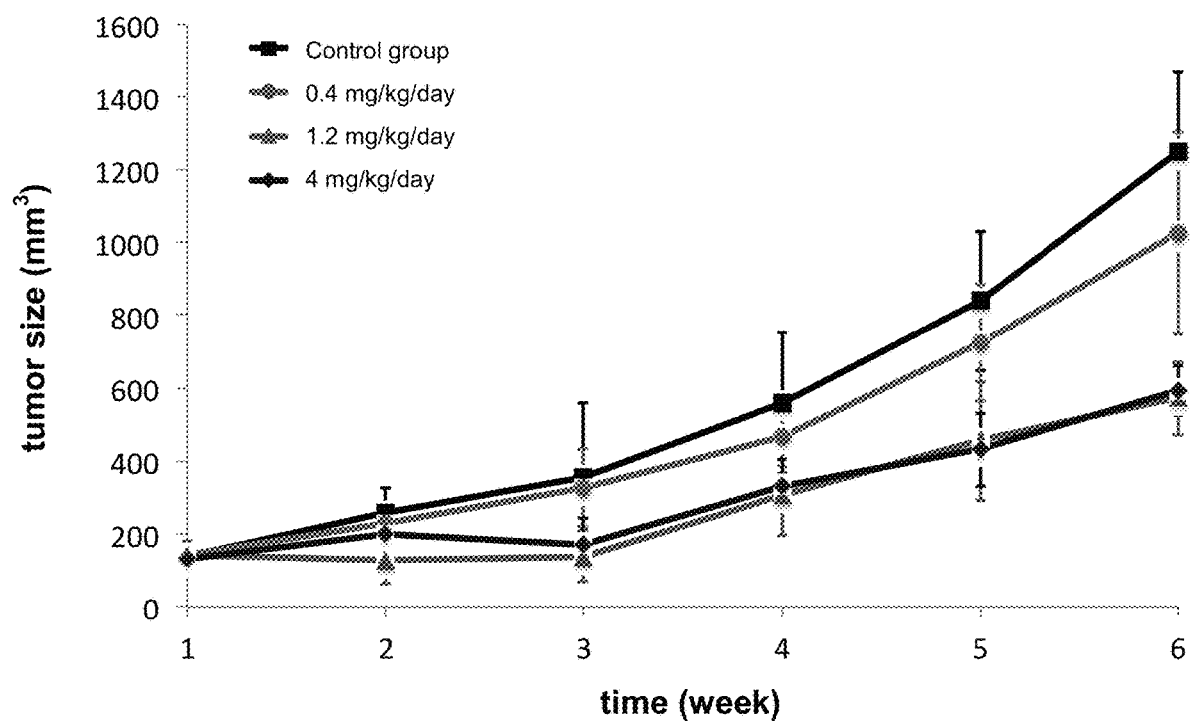
FIG. 1 shows the curve of tumor sizes related to nude mice (BALB/c nu/nu mice) administered with pretreatment of the pharmaceutical composition of various dosages (0.4 mg/kg/day, 1.2 mg/kg/day or 4 mg/kg/day) for 1 week, and then injected with lung cancer cell line.

Other objectives, advantages and novel features of the invention will become more apparent from the following detailed description when taken in conjunction with the accompanying drawings.

The pharmaceutical composition of the present invention comprising ferrous amino acid chelate was used for cancer treatment, and the pharmaceutical composition comprising ferrous amino acid chelate was mixed with a pharmaceutically acceptable carrier as pharmaceuticals for inhibiting or treating cancer. The pharmaceutical composition comprising ferrous amino acid chelate was made from inorganic iron mixing amino acid and went through heating.

In a preferred embodiment of the present invention, the pharmaceutical composition comprising ferrous amino acid chelate further included a reductant, wherein the reductant was ascorbic acid, citric acid, acetic acid, propionic acid, butyric acid, lactic acid, malic acid, sulfonic acid or succinic acid.

In a preferred embodiment of the present invention, the inorganic iron was ferrous sulfate, ferrous chloride or ferrous pyrophosphate, and the amino acid was glycine to form a pharmaceutical composition comprising ferrous amino acid chelate; the pharmaceutical composition comprising ferrous amino acid chelate was proved for inhibiting cancer cell.

Preparation Example 1: Preparation of the Composition Comprising Ferrous Amino Acid Chelate The pharmaceutical composition comprising ferrous amino acid chelate was prepared as follows: firstly, ferrous sulfate and glycine (more than 98% purity) were mixed in a weight ratio of 1:1.3 through 60° C. to 90° C. and heated for 8 hours to 48 hours to obtain the composition comprising ferrous amino acid chelate, wherein the chelating ratio of ferrous and amino acid of the ferrous amino acid chelate was between 1:1 and 1:4, and the concentration of the pharmaceutical composition comprising ferrous amino acid chelate was modulated to 0.1 µg/µl, 0.3 µg/µl, 1 µg/µl or 3 µg/µl.

Preparation Example 2: Culture of Lung Cancer Cell

A549 cells were seeded in DMEM medium containing 10% fetal bovine (FBS), 1% penicillin (100 U/mL)-streptomycin (100 g/ml), 1% glutamine (200 mM) under 37° C. and 5% $CO_2$ about 70% to 80% cell adhesion for subculture.

Preparation Example 3: Culture of Lung Cancer Cell

SK Hep1 cells were seeded in DMEM medium containing 10% fetal bovine (FBS), 1% non-essential amino acid (NEAA), 1% penicillin (100 U/mL)-streptomycin (100 g/ml) under 37° C. and 5% $CO_2$ for 3-4 days subculture once.

Example 1: Volume Measurement of Tumor Cells 0.1 µg/µl, 0.3 µg/µl or 1 µg/µl pharmaceutical composition comprising ferrous amino acid chelate obtained from preparation example 1 were respectively fed to BALB/c nu/nu mice aged 5-6 weeks (purchased from National Laboratory Animal Center, Taiwan) under 0.4 mg/kg/day, 1.2 mg/kg/day or 4 mg/kg/day and sterile water was used as a control group through 7 days. $1 \times 10^7$ cell/ml (100 µl) A549 cells obtained from preparation example 2 were respectively injected to subcutaneous of brachial artery near the hind legs of each nude mouse. After then, tumors size and volume were measured every 7 days with venier caliper, and each nude mouse was sacrificed after 6 weeks.

The tumor volume was calculated as follows:

$$(a \times b^2)/2 (mm^3),$$ wherein "a" was the longest diameter of a tumor, "b" was the shortest diameter.

Figure 2:
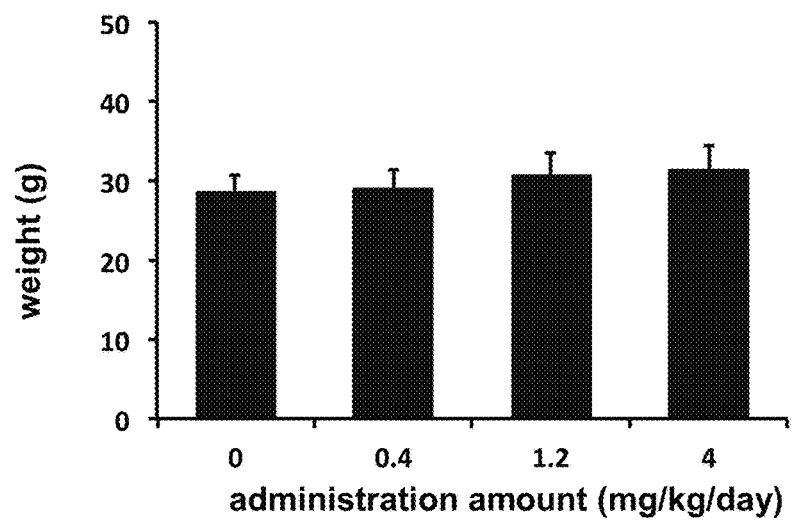
FIG. 2 shows the bar chart related to weight change of nude mice administrated with the pharmaceutical composition comprising ferrous amino acid chelate of the present invention for 6 weeks.

As shown in FIG. 1, the volumes of lung tumors were increasing in coordination with the increasing days, when the dosage of the pharmaceutical composition comprising ferrous amino acid chelate was 1.2 mg/kg/day or 4 mg/kg/day could inhibit tumor volume effectively. As shown in FIG. 2, the growth of the nude mice would not be inhibited via the pharmaceutical composition comprising ferrous amino acid chelate.

4 mg/kg/day pharmaceutical compositions comprising ferrous amino acid chelate obtained from preparation example 1 were respectively fed to SCID mice aged about 6 weeks (purchased from Laboratory Animal Center of National Taiwan University College of Medicine) 5 times a week and sterile water was used as a control group. After 1 week, the SCID mice were anesthetized and exposed to 0.75 Gy radiations. Then, $1 \times 10^7$ cell/ml (100 µl) SK Hep1 cells obtained from preparation example 3 were respectively injected to subcutaneous of near lower back of each SCID mouse. After then, tumors size and volume were measured every 7 days with venier caliper, and each nude mouse was sacrificed after 4 weeks.

Figure 3:
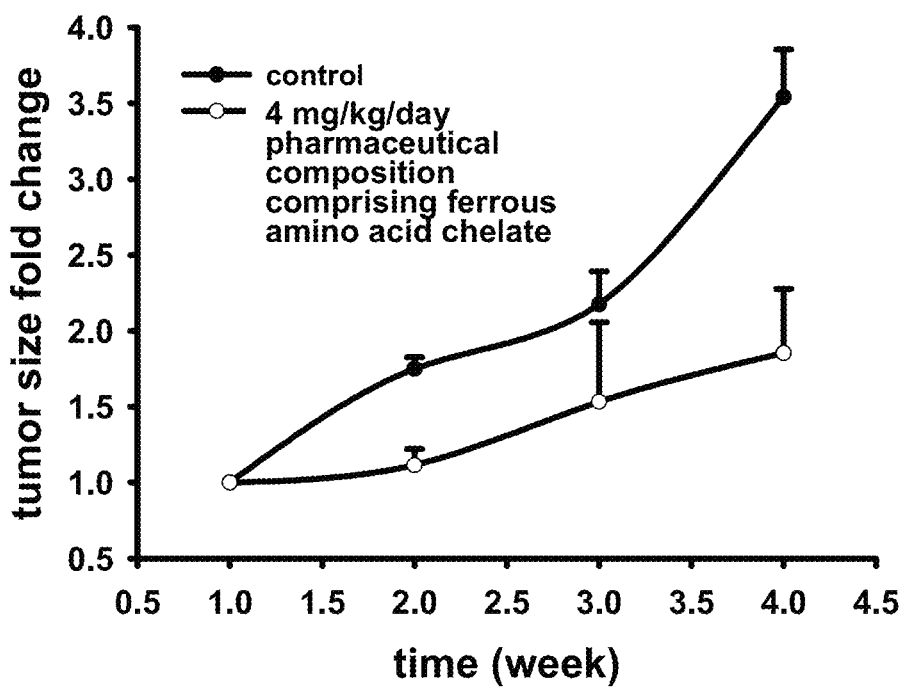
FIG. 3 shows the tumor size fold change curve related to severe combined immunodeficient mice (SCID mice) administered with pretreatment of the pharmaceutical combination for 1 week, and then injected with liver cancer cell line.

As shown in FIG. 3, the volumes of liver tumors were increasing in coordination with the increasing days, and the volumes of liver tumors of the control group were 3.5 times than original tumor size at the fourth week. However, the volumes of liver tumors were only 1.8 times than original tumor size by administering 4 mg/kg/day pharmaceutical composition comprising ferrous amino acid chelate. Accordingly, the pharmaceutical composition comprising ferrous glycinate chelate was able to inhibit liver tumor volume.

Example 2: Analysis of Subject Survival Rate

Figure 4:
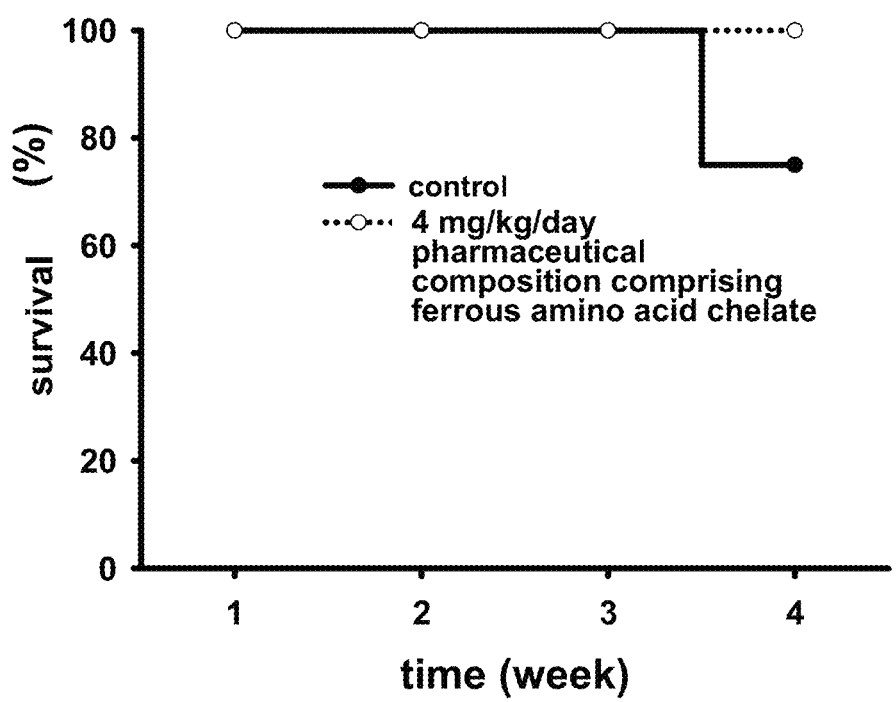
FIG. 4 shows the survival rate curves of SCID mice injected with tumor cells within 5 weeks.

As shown in FIG. 4, the survival rate of the control group was 75% through 4 weeks. Nevertheless, the survival rate of the SCID mice was 75% by administering 4 mg/kg/day pharmaceutical composition comprising ferrous amino acid chelate for 4 weeks. Thus, administering the pharmaceutical composition comprising ferrous amino acid chelate could enhance the survival rate of the SCID mice.

Example 3: Control Experiment of Other Compounds Containing Iron

The nude mice were divided into 5 groups, the control group was administered with phosphate buffered saline (PBS), the first group was administered with 1.2 mg/kg/day pharmaceutical composition comprising ferrous amino acid chelate, the second group was administered with 12 mg/kg/day pharmaceutical composition comprising ferrous amino acid chelate, the third group was administered with 1.2 mg/kg/day Ferrochel® (purchased from Albion Co. Ltd.), and the fourth group was administered with 1.2 mg/kg/day ferrous sulfate (inorganic iron) for 7 days. Then, 1×10⁷ cell/ml (100 µl) A549 cells obtained from preparation example 2 were respectively injected to subcutaneous of brachial artery near the hind legs of each nude mouse. After then, tumors size and volume were measured every 7 days with venier caliper, and each nude mouse was sacrificed after 6 weeks.

Figure 5:
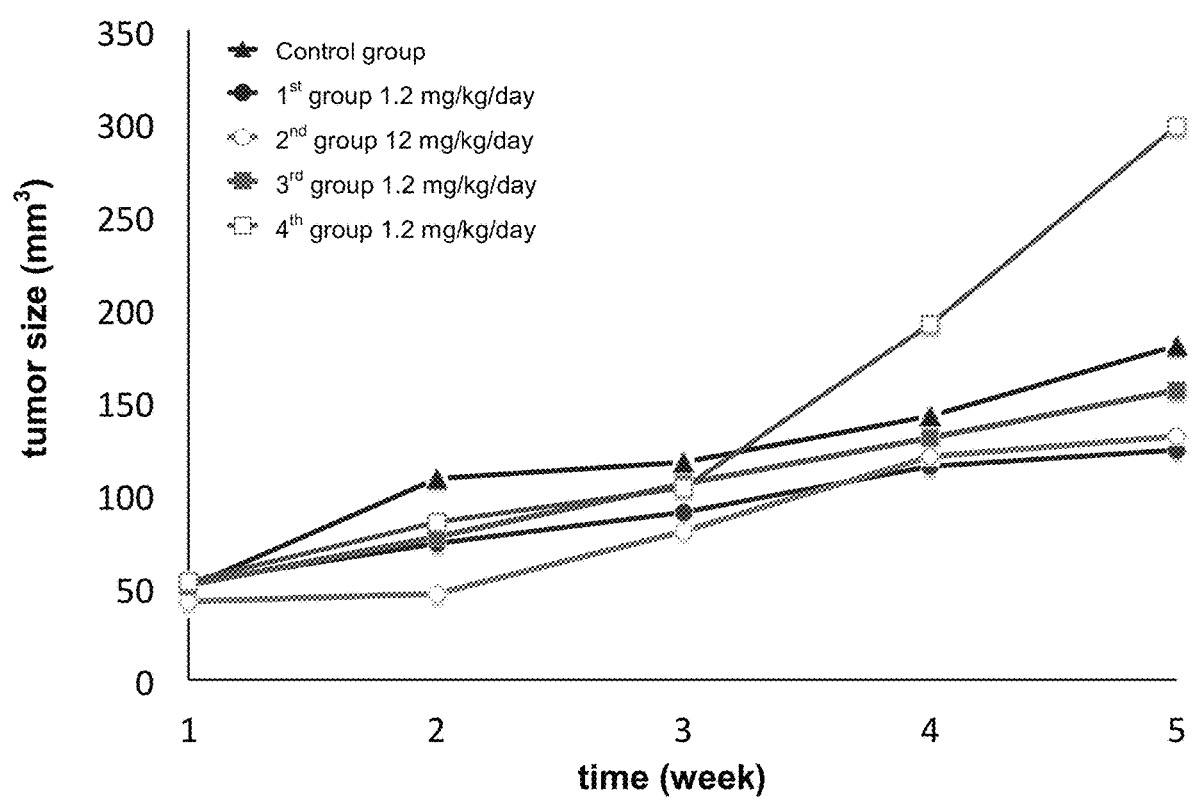
FIG. 5 illustrates that nude mice were divided into five groups, in which the control group was administered with phosphate buffer solution, the first group was administered with 1.2 mg/kg/day pharmaceutical combination comprising ferrous amino acid chelate, the second group was administered with 12 mg/kg/day pharmaceutical combination comprising ferrous amino acid chelate, the third group was administered with 1.2 mg/kg/day ferrous amino acid (Ferrochel®), the fourth group was administered with 1.2 mg/kg/day ferrous sulfate. The nude mice in each group were administered for 7 days, and then lung cancer cells were injected into each mouse.

As shown in FIG. 5, the volumes of lung tumors were increasing in coordination with the increasing days, but the volume of lung tumors of the first and the second group administered with 12 mg/kg/day or 1.2 mg/kg/day pharmaceutical composition comprising ferrous amino acid chelate was better inhibited than the third group administered with Ferrochel® and the fourth group administered with ferrous sulfate.

The nude mice were divided into 5 groups, the control group was administered with phosphate buffered saline (PBS), the first group was administered with 4 mg/kg/day pharmaceutical composition comprising ferrous amino acid chelate, the second group was administered with 12 mg/kg/day pharmaceutical composition comprising ferrous amino acid chelate, the third group was administered with 4 mg/kg/day Ferrochel®, and the fourth group was administered with 4 mg/kg/day ferrous sulfate (inorganic iron) for 2 weeks. Then, 1×10⁷ cell/ml (100 µl) SK Hep1 cells obtained from preparation example 3 were respectively injected to subcutaneous of near lower back of each SCID mouse. After then, tumors size and volume were measured every 7 days with venier caliper, and each nude mouse was sacrificed after 5 weeks.

Figure 6:
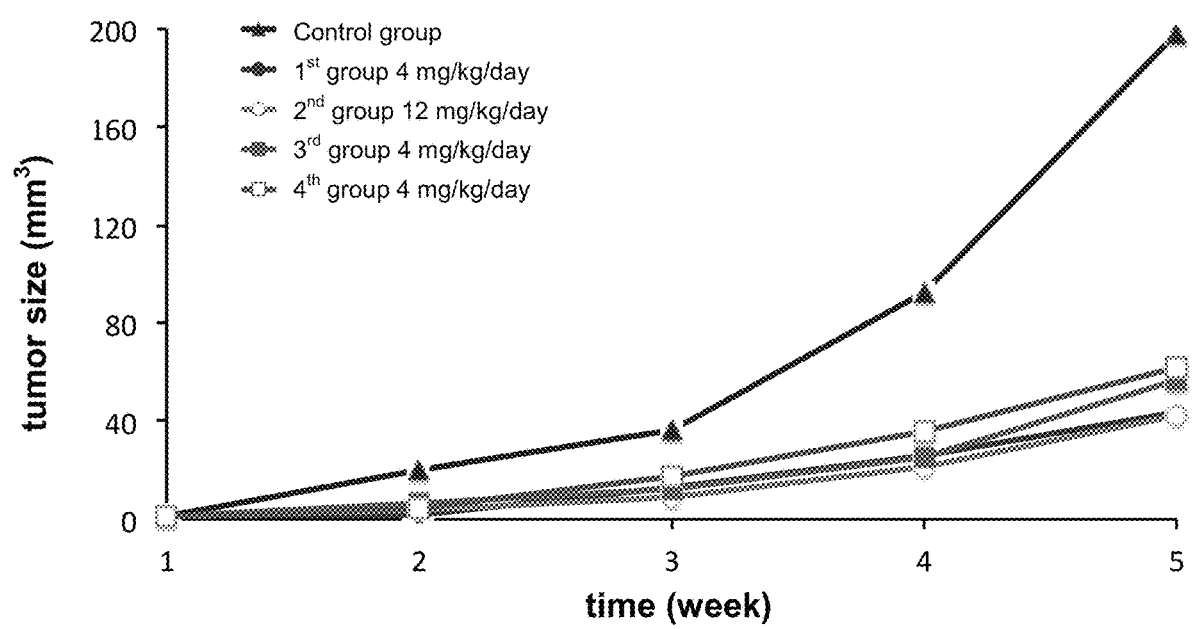
FIG. 6 illustrates that nude mice were divided into five groups, in which the control group was administered with phosphate buffer solution, the first group was administered with 4 mg/kg/day pharmaceutical combination comprising ferrous amino acid chelate of the present invention, the second group was administered with 12 mg/kg/day pharmaceutical combination comprising ferrous amino acid chelate, the third group was administered with 4 mg/kg/day ferrous amino acid (Ferrochel®), the fourth group was administered with 4 mg/kg/day ferrous sulfate. The nude mice in each group were administered for 7 days, and then liver cancer cells were injected into each mouse.

As shown in FIG. 6, the volume of liver tumors of the first and the second group administered with 4 mg/kg/day or 12 mg/kg/day pharmaceutical composition comprising ferrous amino acid chelate was better inhibited than the third group administered with Ferrochel® and the fourth group administered with ferrous sulfate.

What is claimed is:

1. A method for cancer treatment comprising a step of administering to a subject in need thereof a therapeutically effective amount of a pharmaceutical composition comprising a ferrous glycine chelate and a pharmaceutically acceptable carrier; wherein the ferrous glycine chelate is prepared by mixing inorganic iron and glycine and heating through 60° C. to 90° C. for 8 hours to 48 hours to obtain the pharmaceutical composition comprising ferrous glycine chelate, wherein the weight ratio of inorganic iron and glycine is between 1:1.2 and 1:1.5; wherein the cancer is liver cancer or lung cancer, and the ferrous glycine chelate consists of glycine and ferrous iron.

2. The method according to claim 1, wherein the chelating ratio of ferrous iron to glycine in the ferrous glycine chelate is between 1:1 and 1:4.

3. The method according to claim 1, wherein the chelating ratio of ferrous iron to glycine in the ferrous glycine chelate is between 1:1.5 and 1:2.5.

4. The method according to claim 1, wherein the therapeutically effective amount of the pharmaceutical composition is between 0.2 mg/kg/day and 15 mg/kg/day.

5. The method according to claim 1, wherein the therapeutically effective amount of the pharmaceutical composition is between 0.4 mg/kg/day and 12 mg/kg/day.

6. The method according to claim 1, wherein the inorganic iron is ferrous sulfate, ferrous chloride or ferrous pyrophosphate.

7. The method according to claim 1, wherein the pharmaceutical composition includes a reductant, wherein the reductant is ascorbic acid, citric acid, acetic acid, propionic acid, butyric acid, lactic acid, malic acid, sulfonic acid or succinic acid.

8. The method according to claim 1, wherein the pharmaceutical composition is an enteral dosage form.

9. The method according to claim 8, wherein the enteral dosage form is an oral dosage, wherein the oral dosage is selected from the group consisting of solutions, suspensions, tablets and capsules.

10. The method according to claim 1, wherein the pharmaceutical composition is a parenteral dosage form.

* * * * *